US011369810B2

(12) United States Patent
Averkiou et al.

(10) Patent No.: US 11,369,810 B2
(45) Date of Patent: Jun. 28, 2022

(54) METHOD AND APPARATUS FOR ULTRASONIC MEDIATION OF DRUG DELIVERY USING MICROBUBBLES

(71) Applicants: Michalakis Averkiou, Seattle, WA (US); Edward Lam Shang Leen, London (GB)

(72) Inventors: Michalakis Averkiou, Seattle, WA (US); Edward Lam Shang Leen, London (GB)

( * ) Notice: Subject to any disclaimer, the term of this patent is extended or adjusted under 35 U.S.C. 154(b) by 411 days.

(21) Appl. No.: 15/847,217

(22) Filed: Dec. 19, 2017

(65) Prior Publication Data
US 2018/0169444 A1 Jun. 21, 2018

Related U.S. Application Data

(60) Provisional application No. 62/436,021, filed on Dec. 19, 2016.

(51) Int. Cl.
*A61N 7/02* (2006.01)
*A61M 37/00* (2006.01)
(Continued)

(52) U.S. Cl.
CPC ............... *A61N 7/02* (2013.01); *A61B 8/085* (2013.01); *A61M 37/0092* (2013.01);
(Continued)

(58) Field of Classification Search
CPC .... A61N 7/02; A61N 7/00; A61N 2007/0095; A61N 2007/0039; A61N 2007/0078;
(Continued)

(56) References Cited

U.S. PATENT DOCUMENTS 10,232,196 B2 * 3/2019 Soltani ............. A61M 25/0032
2007/0265560 A1 * 11/2007 Soltani ................... A61N 7/022
604/22
(Continued)

OTHER PUBLICATIONS

Sen et al. "Mechanical index". Anatol J Cardiol 2015; 15: 334-6. (Year: 2015).*
(Continued)

*Primary Examiner* — Shahdeep Mohammed (57) ABSTRACT

An ultrasonic therapy system delivers ultrasonic therapy energy to a therapy site in the body which is infused with microbubbles. A system without an image guidance capability has an array transducer which delivers therapy energy, a therapy transducer driver which causes the array transducer to deliver therapeutic energy, a control for controlling the intensity of the therapeutic energy, and a display of the sonotherapy signal strength of the energy and the concentration of microbubbles at the therapy site. A system with ultrasonic imaging capability will display an ultrasound image for therapeutic guidance and a measure of the microbubble concentration. The method of the present invention is performed as an adjunct to a standard drug therapy or other treatment regimen, following such treatment with an infusion of ultrasound and delivery of ultrasound therapy energy.

7 Claims, 7 Drawing Sheets (51) Int. Cl.
*A61N 7/00* (2006.01)
*A61B 8/00* (2006.01)
*A61B 90/00* (2016.01)
*A61B 8/08* (2006.01)
*A61B 34/30* (2016.01)

(52) U.S. Cl.
CPC ............... *A61N 7/00* (2013.01); *A61B 8/46* (2013.01); *A61B 34/30* (2016.02); *A61B 2090/065* (2016.02); *A61B 2090/378* (2016.02); *A61N 2007/0039* (2013.01); *A61N 2007/0078* (2013.01); *A61N 2007/0095* (2013.01)

(58) Field of Classification Search
CPC ... A61B 8/085; A61B 34/30; A61B 2090/065; A61B 2090/378; A61B 8/46; A61B 8/481; A61M 37/0092
See application file for complete search history.

(56) References Cited

U.S. PATENT DOCUMENTS

| | | | | |
|---|---|---|---|---|
| 2008/0045865 | A1* | 2/2008 | Kislev | A61N 7/022 601/3 |
| 2009/0234231 | A1* | 9/2009 | Knight | A61M 37/0092 600/458 |
| 2010/0168569 | A1* | 7/2010 | Sliwa | A61B 8/0841 600/439 |
| 2011/0125080 | A1* | 5/2011 | Shi | A61K 49/223 604/20 |
| 2012/0029397 | A1* | 2/2012 | Chin | A61N 7/00 601/2 |
| 2013/0046229 | A1* | 2/2013 | Konofagou | A61B 17/225 604/22 |
| 2014/0213841 | A1* | 7/2014 | D'Hooge | A61B 8/481 600/1 |
| 2016/0106395 | A1* | 4/2016 | Hynynen | A61B 8/0891 600/431 |
| 2016/0279449 | A1* | 9/2016 | Powers | A61B 8/0833 |
| 2017/0360406 | A1* | 12/2017 | Seip | A61B 8/085 |
| 2018/0049762 | A1* | 2/2018 | Seip | A61B 8/0891 |
| 2018/0071553 | A1* | 3/2018 | Vortman | A61N 7/022 |

OTHER PUBLICATIONS

Lampaskis et al. "Investigation of the Relationship of Nonlinear Backscattered Ultrasound Intensity With Microbubble Concentrationat Low MI". Ultrasound in Med. & Biol., vol. 36, No. 2, pp. 306-312, 2010. Copyright 2010 World Federation for Ultrasound in Medicine & Biology (Year: 2010).*

Senior et al. "Contrast echocardiography: evidence-based recommendations by European Association of Echocardiography". European Journal of Echocardiography (2009) 10, 194-212. doi:10.1093/ejechocard/jep005 (Year: 2009).*

Keravnou et al. Accurate Measurement of Microbubble Response to Ultrasound With a Diagnostic Ultrasound Scanner. IEEE Transactions on Ultrasonics, Ferroelectrics, and Frequency Control, vol. 62, No. 1, Jan. 2015. https://ieeexplore.ieee.org/stamp/stamp.jsp?tp=&arnumber=7002936 (Year: 2015).*

Lampaskis et al. Investigation of the Relationship of Nonlinear Backscattered Ultrasound Intensity With Microbubble Concentration At Low MI. Ultrasound in Med. & Biol., vol. 36, No. 2, pp. 306-312, 2010. http://faculty.washington.edu/maverk/pdf/publications/journals/Lampaskis_UMB_2010.pdf (Year: 2010).*

* cited by examiner

METHOD AND APPARATUS FOR ULTRASONIC MEDIATION OF DRUG DELIVERY USING MICROBUBBLES

This application claims the benefit U.S. Provisional Application Ser. No. 62/436,021, filed Dec. 19, 2016. This application is hereby incorporated by reference herein.

This invention relates to ultrasonic therapeutic systems and, in particular, to the use of ultrasound to mediate the effectiveness of pharmacological and other compounds in the body with the use of microbubbles.

Therapeutic uses of ultrasound have been in varying degrees of use for a number of years. High intensity ultrasound has been used to ultrasonically break up kidney stones, a procedure known as lithotripsy. Recently the same principles have been applied at similar energy levels but different pulse lengths to mechanically destroy pathological tissue, a procedure known as histotripsy. HIFU (high intensity focused ultrasound) is in clinical use today to ablate tissue by ultrasonic heating. Another related use which is sometimes performed at even diagnostically acceptable levels of ultrasound is known as sonothrombolysis, in which ultrasound is used to break up obstructing blood clots. Sometimes this is done in conjunction with drug therapy, as with tPa in the treatment of stroke. It is also known to be mediated with an application of microbubbles. The microbubbles are agitated or destroyed to physically break up a thrombus.

Microbubbles began their use in ultrasound in the 1980's as contrast agents, as their presence would light up an image of vasculature and perfused tissue, both at fundamental and harmonic frequencies. In recent years their use in therapy has been proposed and explored. One of the first therapeutic uses of microbubbles was the transport of encapsulated pharmaceuticals through the bloodstream to a targeted region of the body, then the release of the drugs by rupturing the microbubbles with ultrasound. Recently such microbubbles have been specifically targeted for certain organs by the use of antibody tagging. The therapeutic use of microbubbles to break up a thrombus, sonothrombolysis, has been discussed above. A more recent development as an adjunct to gene therapy is sonoporation, which uses ultrasound to cavitate microbubbles and thereby disrupt the cell plasma membrane and facilitate the mobility of large molecules such as DNA into a cell. The use of microbubbles with the ultrasound has been found to enhance this cellular transfection.

Accordingly it is an object of the present invention to enhance and improve the use of ultrasound to mediate drug delivery. It is a further object of the present invention to enhance the effectiveness of ultrasonic drug delivery through the use of microbubbles in combination with ultrasound.

In accordance with the principles of the present invention, an ultrasonic therapy system and method are described which are used in conjunction with the delivery of microbubbles to a patient to enhance the effectiveness of drug uptake in the body or the delivery of other therapeutic compounds to a specific region of the body. In a basic implementation the therapy system does no ultrasonic imaging but does have controls and display metrics useful in assuring the effectiveness of the therapy. One such metric is one which defines the ultrasonic dose, such as a measure of the intensity of the delivered ultrasound and its periodicity of delivery, and controls for adjusting them. Other metrics are a measure of the sonotherapy signal strength of the ultrasound applied to microbubbles and a measure of the concentration of microbubbles at the target site in the body. When either of these metrics are outside a desired range for the intended therapy, an ultrasonic dose control such as ultrasound intensity, periodicity, or triggering delay can be adjusted to return the therapy to its intended level of effectiveness. When the bubble concentration metric is low, the rate at which microbubbles are administered to the body (typically by infusion) is increased in order to bring the concentration to its intended level. The conditions for effective therapy include an ultrasonic frequency typically in the range of 0.5 to 2 MHz delivered for a period of 10 to 10,000 cycles scanned with a line density (ultrasound beam width) high enough to assure adequate microbubble destruction in the therapy region while avoiding premature destruction in regions of the body not yet scanned. These metrics may also be displayed as an output and controlled by the user, or adjusted in a closed loop feedback control fashion. Placement of the therapy transducer so as to direct the ultrasound toward the therapy site can be aided with a diagnostic imaging system for therapy guidance. Alternatively, the ultrasound can be broadly directed toward a target organ without image guidance, such as by scanning a target organ like the liver. Treatment of the whole liver with ultrasound will produce the intended effect at a specific therapy site within the liver.

In a more advanced implementation, the therapy system of the present invention also includes an imaging capability and hence imaging and therapy are conducted by the system in an interleaved manner. Preferably the ultrasound for both imaging and therapy is delivered by the same ultrasound probe, which may have specific transducer elements for therapy and other specific transducer elements for imaging. A transducer probe with a split transducer aperture may be used, for instance. In a preferred embodiment the system display screen displays two ultrasound images of the target region, one a low MI (mechanical index) fundamental frequency for navigation and image guidance of the procedure, and the other a low MI microbubble-specific (e.g., harmonic) frequency image of the microbubble field surrounding the therapy site. The latter image visually guides the user as to the sufficiency of the microbubble concentration for effective therapy. The advanced system may also contain the metrics and controls of the basic system. Another display technique is to acquire and display a low MI fundamental frequency image of the therapy site, then acquire and display a microbubble-specific frequency triggered image of the microbubble cloud in the microvasculature when interrogated with the therapy pulses, i.e., a high MI microbubble image. This triggered image acquisition is followed by a period of therapeutic ultrasound delivery. Yet another alternative is to perform real-time low MI fundamental frequency imaging of the therapy site for treatment navigation and display of the sonotherapy signal strength and the microbubble concentration metrics. An image will also preferably have a cursor or box by which a user designates the therapy target in the imaged anatomy. The therapy ultrasound is then delivered to the region designated by the user.

Either system can also employ a robotic arm to hold the therapy or imaging/therapy probe in contact with the patient during therapy. The robotic arm can be fully manual and adjusted for best placement by the user, or it can be automatically controlled by a feedback control unit to continually aim the therapy ultrasound beams at the therapy target region while maintaining the therapy indices within an optimal range.

The therapy or imaging/therapy probe is preferably a curved-linear array transducer probe. In the simplest implementation, the therapy probe may be a single element transducer designed for specific ultrasonic dose delivery in a fixed area around its axis. For the more advanced imaging/therapy probe a split aperture array uses one sub-aperture for imaging and another sub-aperture for therapy, with beam steering from each sub-aperture to the treatment site. For therapy, a large aperture with high focusing gain is used when the therapy protocol calls for focusing the ultrasound at the therapy site. Another therapy protocol is to sweep the beams over the entire organ being treated. Specific anatomies can use specific transducer types. For instance curved-linear and phased array transducers can be used for the liver, whereas linear array transducers can be used for the breast and other shallow targets. A 2D array transducer is most preferred, as this allows the beams to be steered to scan in three dimensions in the body for imaging and/or therapy.

In a method of the present invention a patient is first treated with a pharmacological or other medical treatment compound, following protocols typically or specifically employed for the compound. For instance, if the compound is a chemotherapy drug for a cancer patient, the patient is treated in accordance with a standard chemotherapy treatment protocol. Following the drug treatment regimen, the patient is infused with a microbubble solution. The microbubbles can be delivered by an infusion pump or syringe pump that may be controlled by the therapy system so that a fresh supply of microbubbles is delivered to the patient throughout the ultrasound treatment. Once a desirable microbubble concentration is present at the therapy site, intermittent therapy pulses are delivered to allow fresh microbubbles to flow to the site between pulses. The therapy pulses may be triggered once every two seconds, for example. This therapy continues for a specified time of therapy such as ten minutes to an hour. At the conclusion of the therapy the delivery of therapeutic ultrasound and the infusion of microbubbles is ended. The above procedure is repeated a number of times during the course of chemotherapy at intervals appropriate for the specific disease condition.

Figure 1:
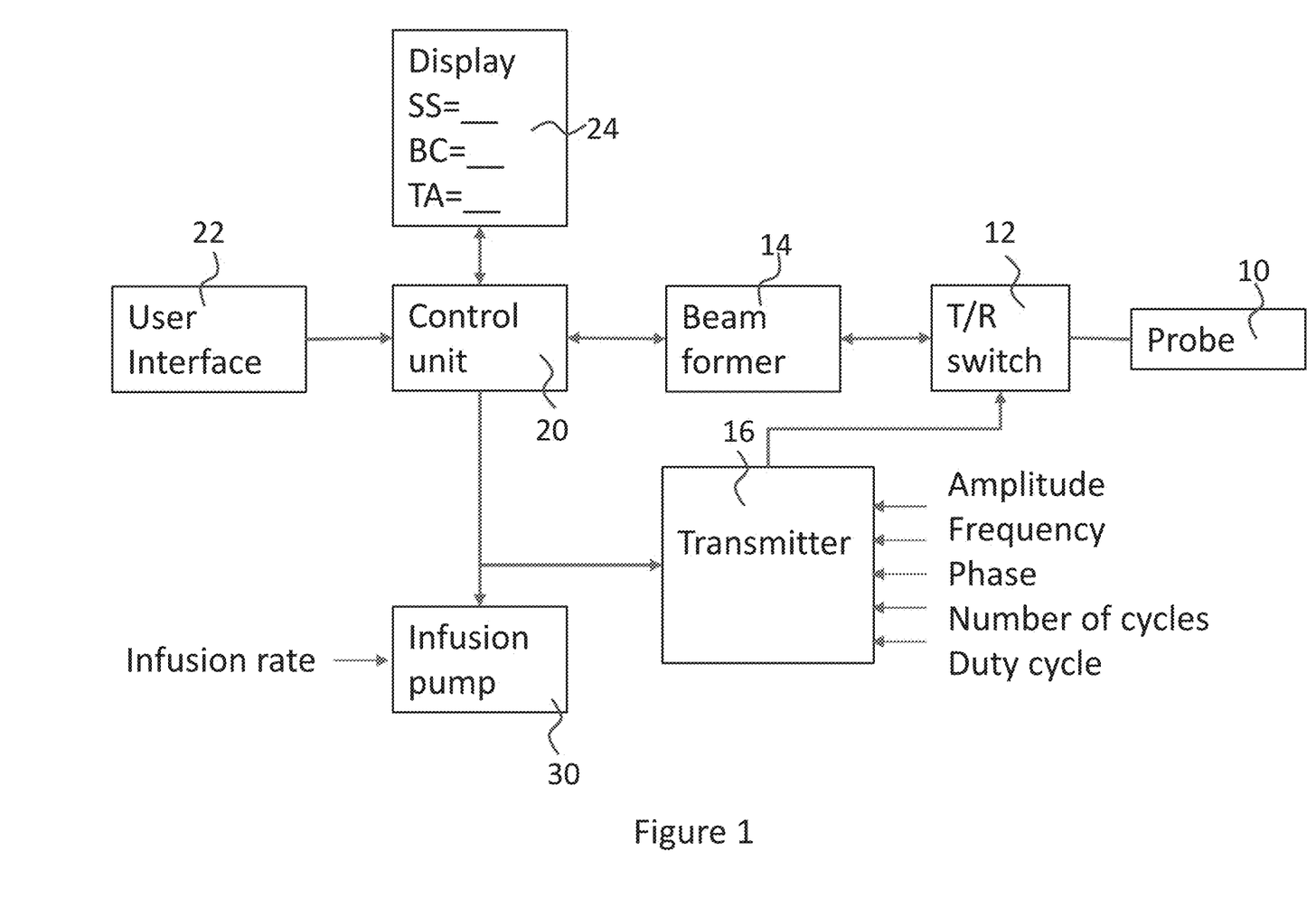
FIG. 1 illustrates in block diagram form a basic therapy system of the present invention which displays therapy indices but does not have an anatomical ultrasonic imaging capability.

Referring first to FIG. 1, a basic system for providing therapy in accordance with the present invention but without image guidance is shown in block diagram form. An ultrasound probe 10 is provided which transmits therapeutic ultrasound. The probe contains an array transducer of elements which transmit ultrasound waves or form beams and receive echo signals in response which are processed by the system. The array can be a one dimensional array or a two dimensional array of piezoelectric transducer elements and can be operated in either a linear or a phased mode of operation. A two dimensional array is preferred for its ability to electronically steer beams in three dimensions. A one dimensional array is constrained to azimuthal scanning in a plane. For deeper abdominal procedures such as treatment of the liver a curved array is often preferred. U.S. Pat. No. 8,551,004 (Adams et al.) describes a suitable curved array and U.S. Pat. No. 6,102,860 describes a curved two dimensional array probe. The probe is connected to the system through a transmit/receive switch 12, which protects sensitive receive components from high transmit voltages. The elements of the array of probe 10 are energized for transmission by a transmitter 16 with drive channels coupled to the elements of the array transducer. As is known in the art, the timing of the applied transmit waveforms to the individual elements provides the ability to steer and focus transmit beams produced by the array transducer. The transmitter 16 is responsive to a number of control parameters, controlled by a control unit 20, which determine the characteristics of the transmitted therapy beams, including the intensity of the beams controlled by the amplitude of the drive signals, the frequency components of the transmit beams, phasing of the transmitted waves, the number of cycles of a transmit pulse, and the duty cycle of the transmit pulses, that is, the time interval between discrete transmit pulses. The transmitter may operate in conjunction with the beamformer 14, the beamformer providing timing for actuation of individual transducer elements which steers and focuses transmit beams at desired locations. For therapy, in accordance with the present invention the transmit pulses will generally be low ultrasonic frequencies below 2 MHz and will be long pulses of many cycles lasting for durations of milliseconds.

The therapy pulses produced by the probe oscillate or break up microbubbles in the scanning field in front of the array in the body of a patient. The microbubbles will scatter ultrasonic energy in response to the transmitted waves, which is received as echo signals by the elements of the array and converted to electrical signals by the piezoelectric elements. The electrical echo signals are coupled to a beamformer 14 by the T/R switch 12. The beamformer operates in the conventional manner to apply relative delays to the echo signals received by the elements, then sums the delayed signals to form coherent echo signals from points and beam directions in the scanning field. The therapy pulse intervals may be interleaved with lower power and shorter duration probing pulses, which produce echoes that are used to calculate the therapy metrics as discussed below.

The coherent echo signals are coupled to the control unit 20 which detects and measures several characteristics of the signals. One characteristic that is detected is the nonlinear frequency components of the echo signals. Cells and tissue in the body will return echo signals which have a primary frequency which is the same as that of the transmitted ultrasound, referred to as the fundamental frequency. These echo signals will have very little nonlinear (e.g., harmonic) frequency components. Echoes returned from microbubbles however will have significant nonlinear signal content. The nonlinear signal content of echoes returned from spatial locations in the scanned field are measured and recorded and this information is used to display two parameters of the therapeutic effect, the sonotherapy signal strength (SS) of the transmitted therapeutic energy and the microbubble concentration (BC) within the scanned field. A third parameter which can be user-controlled, measured and displayed is the therapeutic amplitude (TA) of the transmitted ultrasound. The system may use the Mechanical Index (MI) value typically used for ultrasonic imaging as the displayed TA value or use acoustic pressure calculated in units of MPa. A typical range of values can be MI ranging from 0.5 to 5.0 (and thus possibly exceeding the maximum value of 1.9 allowed for diagnostic imaging), or MPa ranging from 0.5 MPa to 5.0 MPa (assuming a frequency of 1 MHz). These parameters are calculated by the control unit 20, a computer-based unit programmed to perform the following operations. To measure SS and BC, the nonlinear content of the echoes received from the spatial locations of the scanned field are separated from the fundamental content. This can be done on a frequency basis when the harmonic content of the echoes, such as the nonlinear second harmonic content, is used to measure microbubble characteristics. The control unit then separates the second harmonic content of echoes from each spatial location by filtering the signals to separate signals of a frequency $2f$, where f is the fundamental frequency of the transmit waves. Filtering may be performed by an FIR filter in the control unit, for instance. The second harmonic content is extracted and measured for each spatially discrete echo signal location. Each discrete beam produced by the beamformer 14 is received along a discrete direction in the scanned field, and echoes are received along the depth of field of each received beam, providing the necessary spatial delineation. Another way to separate the nonlinear content, applicable for the imaging aspects of the present invention, is to perform a two-pulse scan of successive, differently modulated transmit beams in each beam direction. The echoes received from corresponding locations in response to the two transmit beams are combined to cancel the linear content and reinforce the nonlinear content of the combined signals, a process known as pulse inversion or amplitude modulated separation. See U.S. Pat. No. 5,706,819 (Hwang et al.) and U.S. Pat. No. 5,577,505 (Brock Fisher et al.)

The SS is measured by detecting the maximum intensity (amplitude) of the nonlinear signals received from a specified area of the scanned field. In the absence of image guidance, the specified area is pre-determined, such as a 4 $cm^2$ area in the center of the scanned field. The units of SS can be millivolts or pressure (Pa), but are generally displayed in normalized values ranging from zero to one. The range can be represented nonlinearly by log compression of the maximum intensity value to display a logarithmic (nonlinear) range. The maximum value of the (nonlinear) signal intensity is displayed as the SS value on a display unit 24 of the system. The SS value gives the user a good indication of whether the microbubbles are being oscillated vigorously or not. This value will be application and patient specific but typically a value of 0.5-1.0 will be assumed to be in the target range. The BC value is measured by calculating the average nonlinear signal intensity of the signals received from a specified area of the scanned field. This may be done by summing the (nonlinear) signal intensities over a specified region such as that used for the SS measurement, then dividing the sum by the area or number of spatial locations of the specified region to produce a measure of the per-unit-area (or per pixel) bubble concentration BC. The calculation for BC is thus the summation of the microbubble backscatter over a specified area divided by the total area, and may be displayed in units of millivolts per $mm^2$. A normalized logarithmically compressed value from zero to one may also typically be used here. This value will also, like the SS value, be application and patient specific but typically a value of 0.5 will be assumed to be in the middle of an acceptable range (0.4-0.6).

Another control parameter which may be made available for more advanced users is the line density (LD). When the ultrasound array probe applies ultrasound therapy by scanning the therapy region with adjacent steered and focused ultrasound beams, the format commonly used for imaging arrays, the therapy system is programmed to transmit a preset number of beams (e.g., 100 or 128 beams) evenly distributed across the therapy region. The beam pattern will be radial with the beam centers spaced apart by a preset number of degrees when sector scanning is used, and parallel to each other and spaced apart by a preset number of millimeters when linear scanning is used. The programming will commonly adjust the beam center spacing automatically when the amplitude of the transmitted ultrasound (TA) is adjusted, increasing the spacing when the amplitude is increased and vice versa. The system may also be implemented with a manual control for LD, enabling the user to vary the line spacing from the programmed algorithm. When a manual LD control is present, the control setting is displayed for the user on the display 24 along with the other therapy parameters. Preferably the displayed value is a normalized representation of the variance from the preset default setting. For instance, an LD value of 0.5 indicates that only half as many lines as nominal are being transmitted (the line spacing is increased), and an LD value of 2.0 indicates that twice as many lines as nominal are being transmitted (the line spacing is decreased). The normalized LD setting is applied as a scaling factor to the normal spacing algorithm, so as the amplitude TA is adjusted, the beam center spacing will continue to change, but more or less than the normal spacing in accordance with the LD scaling factor. The LD control thus enables the user to make fine adjustments to the nominal line spacing, scanning the therapy region with a more dense or less dense pattern of therapy beams.

During therapy the clinician monitors the parameters of the display 24 to maintain a steady oscillation or disruption of microbubbles at the treatment site in the body and a uniform amount of microbubbles to be stimulated by ultrasound. If the bubble concentration (BC) declines below an acceptable level, for instance, the user (or the control unit automatically) can adjust the flow control of the infusion pump 30 which is supplying the microbubble solution to the patient. Increasing the flow of microbubble solution provided by the infusion pump will increase the bubble concentration (BC). If the BC increases above the target range (e.g., >0.6), too many microbubbles are present in the body, and those in the near field will absorb much of the acoustic energy intended for a deeper therapy region, a phenomenon known as acoustic shadowing. In that case, the flow of microbubbles is decreased to reduce the BC. Preferably the application of the ultrasound therapy is triggered to provide intervals without insonification when a fresh supply of microbubbles can flow to the therapy region. After time has been allowed for an influx of new microbubbles, the ultrasound therapy is resumed, and the therapy parameters are updated and displayed for each sonification interval.

For example, the user first sets TA=0.1 (assuming TA=MI) in order to measure BC. BC is always measured with low amplitude transmit energy and before the actual sonoporation procedure starts, such as the probing pulses described above. The user then observes on the display, for instance, that BC=0.3. In response, the infusion rate is increased until BC=0.5. Once BC is in the target range, TA is changed to 1.0 (therapeutic range) which in turn may result, for instance, in SS=0.4. Now TA is further increased to TA=1.5 until SS=0.7. Now both therapeutic indices are within optimal range and the therapy procedure may begin. Another example would be to set TA=0.1 in order to measure BC and then observe on the display that BC=0.9. Then the infusion rate is decreased until BC=0.5. Once BC is in the target range, TA is changed to 2.0 (therapeutic range) which in turn may result, for instance, in SS=0.8. Now both therapeutic indices are within optimal range and the therapy procedure may begin.

A number of the system elements described above are also shown and described in my U.S. Pat. No. 8,460,194 (Averkiou et al.), including an ultrasound probe, T/R switch, transmitter, beamformer, display, a nonlinear signal separator, and a nonlinear signal combiner which produces separated nonlinear signals.

Figure 2:
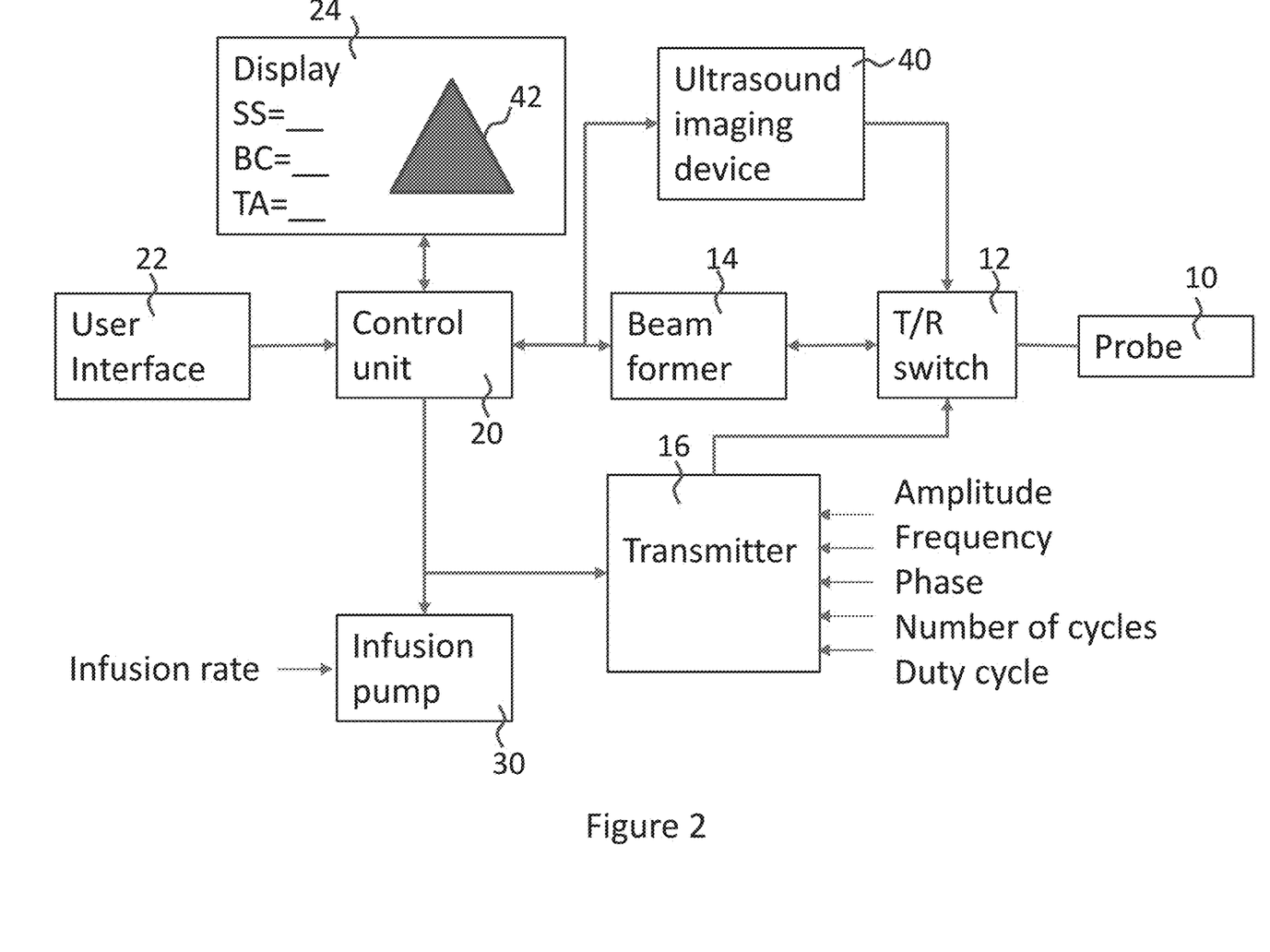
FIG. 2 illustrates in block diagram form an advanced therapy system of the present invention with an imaging capability.

A second implementation of my invention is shown in FIG. 2, in which elements previously shown and described in FIG. 1 are shown with the same reference numbers. The system of FIG. 2 has an ultrasound imaging device 40 which provides image guidance during the therapy procedure. The ultrasound imaging device processes the echo signals produced by the probe 10 to produce a two- or three-dimensional spatial ultrasound image as is known in the art and displays the ultrasound image 42 on the display 24, together with the previously-described therapeutic parameters. A typical imaging device will have a transmit beamformer to transmit steered and focused (or planar) ultrasound beams over the therapy region, a receive beamformer to form coherent receive beams from received echo signals, a signal processor to filter, separate, and detect desired echo signals for imaging, and an image processor with a scan converter to produce an image of the desired display format. The ultrasound image is displayed on the display 24. A suitable ultrasound imaging device is shown and described in my U.S. Pat. No. 8,460,194 (Averkiou et al.) Since the single probe 10 in FIG. 2 is used for both imaging and therapy it preferably has a split aperture with some transducer elements specifically tailored for imaging and other elements specifically tailored for therapy. For instance, the split aperture probe may be a curved array probe useful for abdominal procedures, with smaller, higher pitch elements of one sub-aperture used for imaging at higher frequencies, and the therapy sub-aperture comprised of bigger elements of larger pitch for the lower frequencies and higher power used for therapy. U.S. Pat. No. 8,551,004 (Adams et al.) illustrates a curved array split aperture probe, for example. Preferably electronic beam steering is used in each aperture so that therapy and imaging beams can be steered where needed and high gain focusing of the therapy beams is facilitated. The ultrasound image is displayed in one of several formats as described below, and can be a high or low MI (mechanical index) image, a fundamental or a nonlinear harmonic image. The clinician can thus observe the therapy site in the body in the image as well as the concentration of microbubbles at the site, visually confirming what is indicated by the therapy parameters.

When the system includes an ultrasound imaging device, the user is able to mark or outline the therapy region in the image. The user can trace or place a preset shape (circle, square) over the therapy region, for instance. The control unit 20 can then use the user-outlined region as the specified region to use for the SS and BC calculations.

Figure 3:
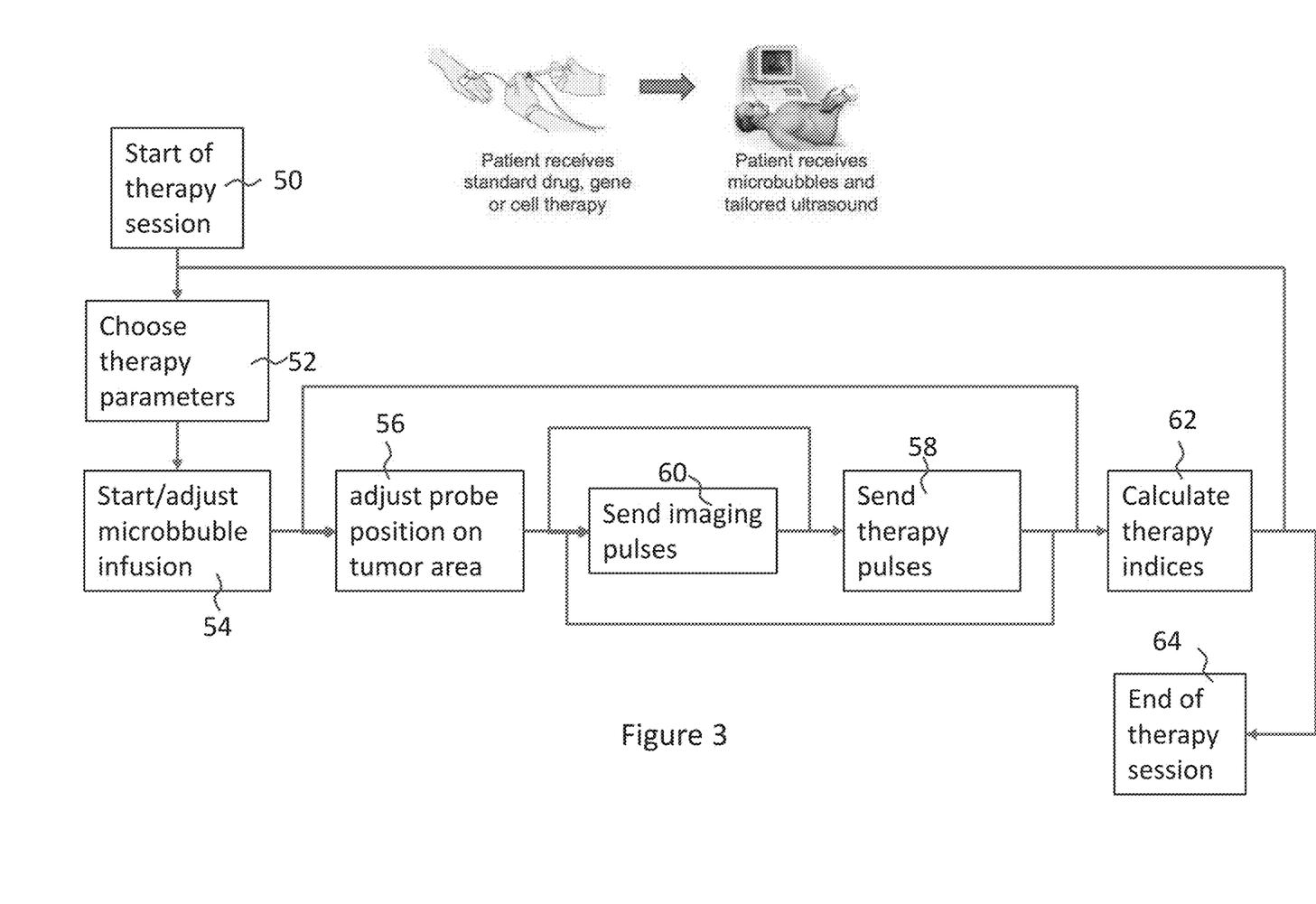
FIG. 3 is a flowchart of a method of the present invention.

FIG. 3 illustrates an ultrasound mediated therapy procedure of the present invention. In this procedure the ultrasound therapy is used as an adjunct to a standard drug, gene, or cell therapy treatment. The treatment could be chemotherapy designed to shrink tumors in the liver, for instance. As shown at the top of the drawing, the patient first receives a standard drug, gene, or cell therapy treatment in accordance with the protocol usually used for the treatment. At the conclusion of the chemotherapy treatment the ultrasound therapy starts with an administration of microbubbles to the patient. The microbubbles can be gas-filled microbubbles or can encapsulate a pharmaceutical which is released when the microbubbles are ruptured at the therapy site to provide medication at the site. The ultrasound therapy is started at 50 and the clinician chooses the therapy parameters to be maintained during ultrasound administration at 52. For instance, a typical selection of therapy parameters could be an ultrasound frequency=1.5 MHz, phase=0, sonoporation pulse of 500 cycles at 5% duty cycle, and with TA=1.5. Then the clinician starts an infusion of a microbubble solution at 54 or adjusts the flow if started previously. The position of the probe against the body of the patient is adjusted at 56 so that the direction of insonification is aimed at the region of the tumor being treated. When the therapy system has image guidance as does the implementation of FIG. 2, imaging pulses are transmitted to the therapy site at 60 and the ultrasound imaging device produces an image of the therapy site which is shown on the display 24. The clinician can use the image to guide the probe position and the delivery of the therapy. Then the probe and system send therapy pulses at 58 to break or stimulate oscillation of the infused microbubbles at the therapy site. Echoes received in response to the therapy pulses are used at 62 to calculate the therapy indices which are displayed to the clinician. In response to this display the clinician can choose new therapy parameters at 52 or adjust one or more of the controls on the user interface 22, shown in FIGS. 1 and 2, to bring the therapy indices into desired ranges for the intended therapy. After the requisite time for the therapy, which may be in the range of 10 minutes to an hour for chemotherapy enhancement, the ultrasound therapy session is ended at 64 by terminating the infusion of microbubbles first and the delivery of ultrasound therapy thereafter. It is sometimes preferred to continue the delivery of ultrasound for another five minutes to ensure that all microbubbles in the body have been activated and subsequently destroyed.

Since holding an ultrasound probe stationary against the body for upwards of an hour can be tiring, it is desirable to use a robotic arm when available to hold the probe against the patient's body. Such a robotic arm can be no more than a mechanical probe holder which holds the probe in the same position against the patient. A Mitsubishi PA-10 industrial robot with a force controller has been used for such applications, for instance. The clinician will monitor the arm to see that the probe does not lose contact with the patient or become mis-directed due to movement by the patient. A preferred robotic arm is one which uses feedback to automatically maintain the proper patient contact and aiming. For instance, successive images acquired by the probe can be compared by block matching to see that they remain in registration, which will be the case when there is no movement of the probe or patient. If temporally different images become out of registration by a predetermined amount, such as one centimeter, the clinician can be alerted to investigate the probe or the robotic arm, when capable, can move the arm to bring successive images into anatomical registration and the target site in the body at or near the center of the image. The PA-10 robot controlled by a Star-Kalman algorithm for image tracking can perform such automatic maintenance of probe positioning. See "Image-Guided Control of a Robot for Medical Ultrasound" by Abolmaesumi et al., *IEEE Trans. Robotics and Automation*, vol. 18, no. 1 (February 2002).

Figure 4:
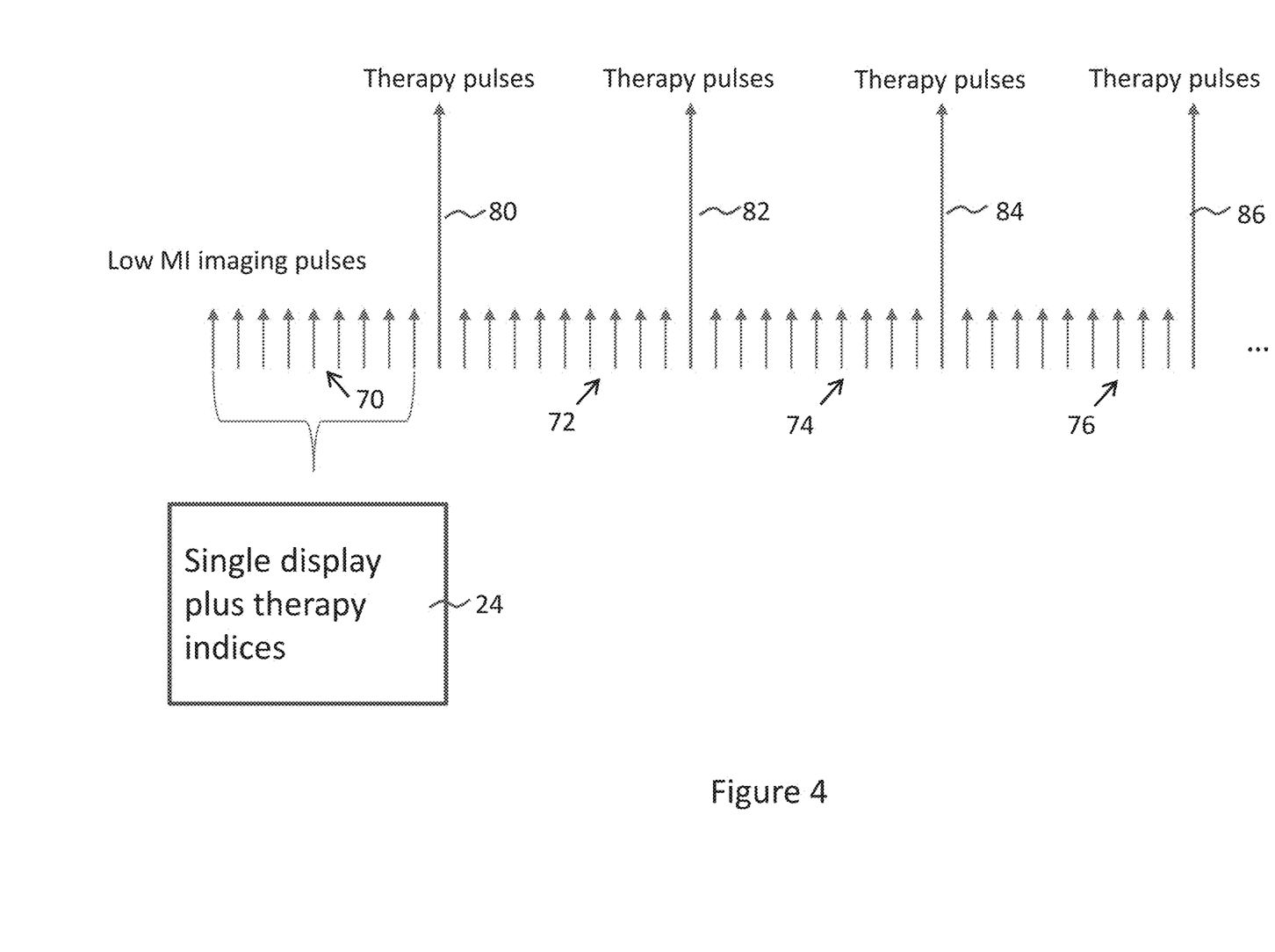
FIG. 4 is a depiction of an ultrasonic imaging configuration of the present invention with a single ultrasonic image display together with a display of therapy indices.

FIG. 4 illustrates one technique for interleaving transmit pulses for ultrasound therapy and imaging in accordance with the present invention. The illustrated pulse sequence is used when the ultrasound therapy system has ultrasound imaging capability as in the case of the system of FIG. 2 and one anatomical ultrasound display is desired. In this example the probe and system transmit a series 70 of spatially discrete low MI (mechanical index) imaging pulses to update some or all of an ultrasound image. This series of imaging pulses is interrupted by the delivery of therapy pulses 80 directed toward the therapy site in the body. Echoes received in response to the therapy pulses are processed as described above to calculate the therapy indices for display to the clinician. After a sufficient period of therapeutic insonification another series 70 of imaging pulses is transmitted to acquire echoes for another portion of or an entire ultrasound image. The interleaving of imaging and therapy continues in this manner, interrupting the imaging pulses 72 for therapy pulses 82, then imaging pulses 74, then therapy pulses 84, followed by imaging pulses 76 then therapy pulses 86, and so on. The echoes produced in response to the imaging pulses are used to display a single image along with the therapy indices on the display 24. The single image is constantly updated and used to guide the delivery of the therapy.

Figure 5:
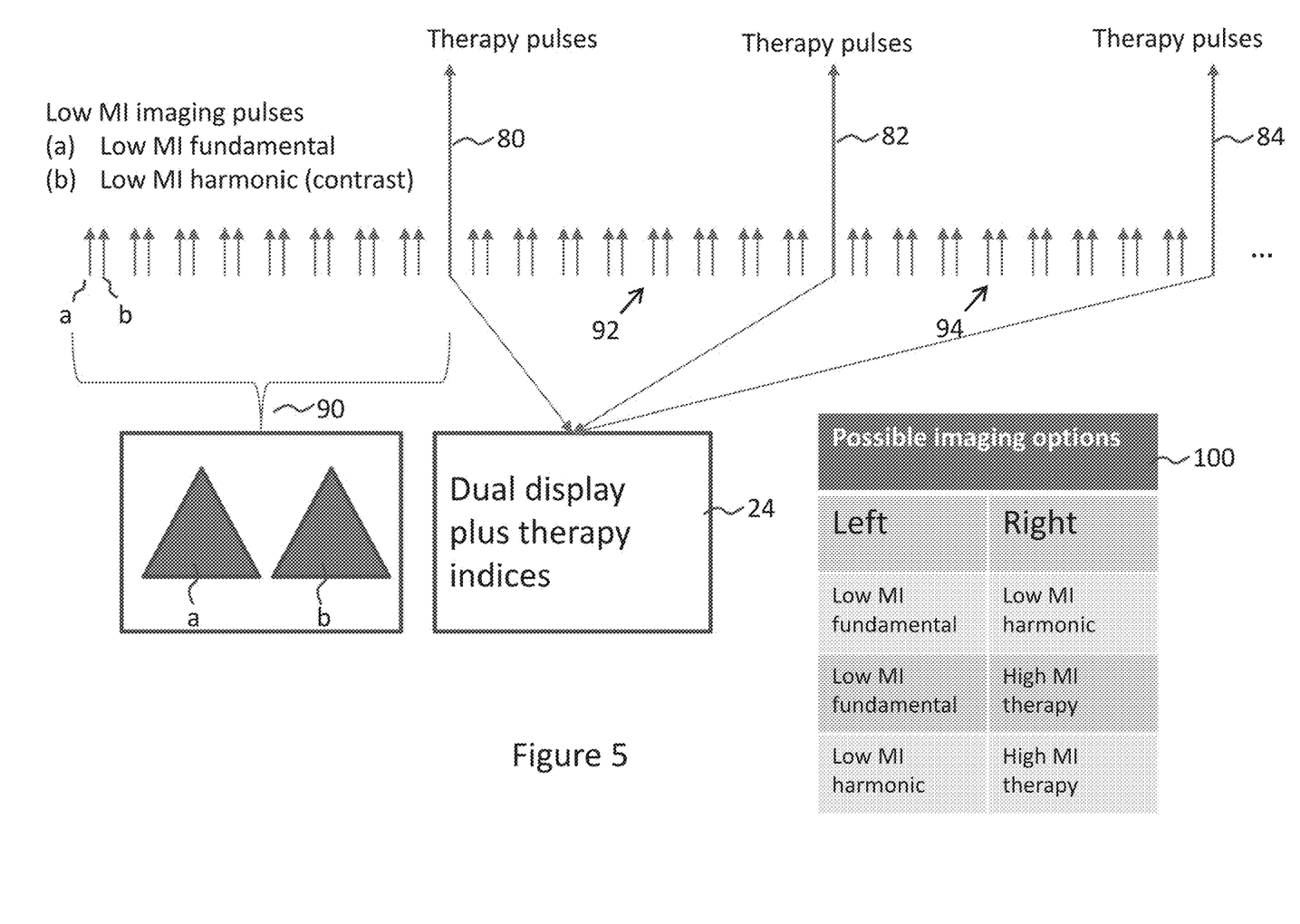
FIG. 5 is a depiction of ultrasonic imaging configuration parameters and variations in accordance with the present invention, illustrating a dual image display together with a display of therapy indices.

FIG. 5 illustrates another imaging format which is interleaved with therapy, this one producing multiple ultrasound images. Preferably the two images are displayed side-by-side on a display 24' as shown by images (a) and (b). These images have different image characteristics and are produced by pairs of transmit pulses (a) and (b). In this example pulse (a) is a low MI imaging pulse in response to which fundamental frequency echoes are received for the production of a fundamental frequency tissue image of the therapy site. The second pulse (b) is a low MI pulse which produces harmonic frequency echoes for the display of a contrast image of the microbubbles at the therapy site. The fundamental image and the harmonic image can be displayed side-by-side as in this illustrated example or can be overlaid in anatomical registration in a single image. Alternatively, only a single pulse can be transmitted and its echoes separated into fundamental and harmonic components as described above to produce the (a) and (b) images at twice the frame rate of display. After a series 90 of imaging pulses have been transmitted, therapy pulses 80 are transmitted to break or stimulate the oscillation of the microbubbles at the therapy site. Echoes received in response to the therapy pulses are processed to calculate the therapy indices, enabling a common display of the two anatomical ultrasound images and the therapy indices as shown by display 24. Successive imaging pulse series 92, 94 and interleaved therapy pulses 82, 84 are transmitted and echoes received to provide continuous ultrasound therapy by stimulation of the microbubbles and updated images of the therapy site and microbubbles as well as the therapy indices for the duration of the therapy.

While the foregoing example shows the dual anatomical images as low MI fundamental and harmonic images, other combinations are possible as illustrated in the table 100 at the lower right of the drawing. A second option is to show one of the images (left, in this example) as a low MI fundamental image, while the other (right) image is a high MI therapy image produced from echoes received in response to high MI therapy pulses. This image combination shows the anatomy where the therapy is taking place, and an image of the effect of the applied therapeutic pulses. Yet another option is for one image (left, in this example) to be a low MI harmonic image while the second (right) image is a high MI therapy image. With this image combination the clinician can distinctly see the cloud of microbubbles at the therapy site in the left image, then the effect of ultrasonic therapy on that cloud in the right image.

The following two flowcharts illustrate therapeutic procedures in accordance with the present invention, one using a single-element transducer and the other using an array transducer. The important control parameters for the two procedures are the infusion rate IR and the therapeutic amplitude TA for both, the pulse repetition frequency PRF for the single-element transducer, and the frame rate FR and line density LD for the array transducer. The main therapy indices that are displayed on the system display are the sonotherapy signal strength SS, which is the maximum signal strength (maximum backscattered signal) in the therapy region of interest (ROI), and the bubble concentration BC, which is the sum of all signals from all pixels in the therapy ROI divided by the total number of pixels in the ROI.

Figure 6A:
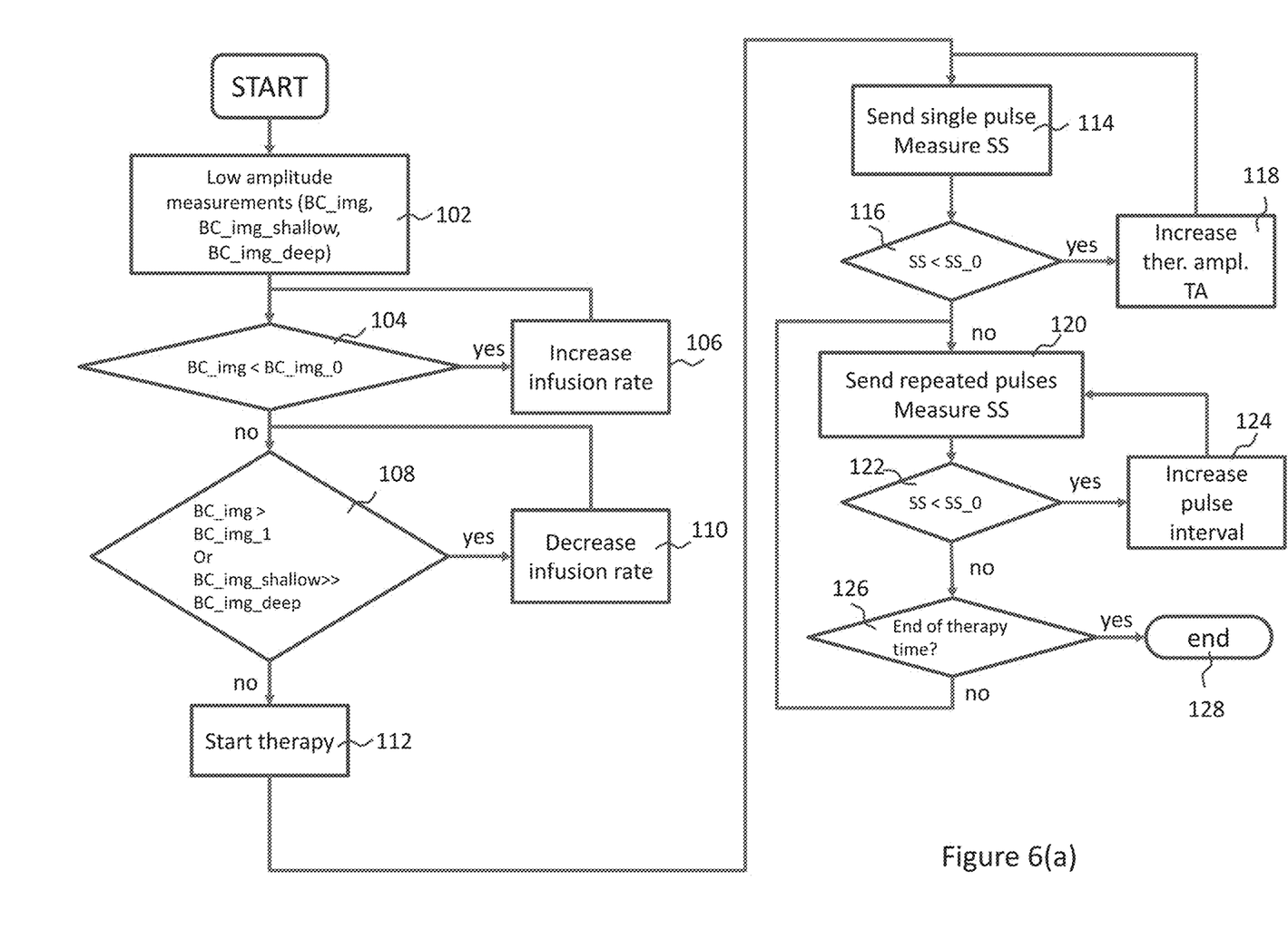
FIG. 6(a) is a flowchart of a therapy procedure conducted in accordance with the principles of the present invention when the probe is a single element transducer probe.

In summary, in the procedure with the single-element transducer, the user first optimizes the infusion rate IR under low MI transmit conditions until the bubble concentration at the therapy ROI (BC_img) is at a favorable level. The therapy is then commenced, initially using a default TA. A single therapy pulse is transmitted by the single-element transducer and SS is measured. Since the transducer has only a single element, the pulse will travel in a line straight in front of the transducer element, with the focal properties of the transducer, which may be narrowly or more broadly focused by the curvature of the transducer element or a lens material as is known in the art. If the SS is low, TA is increased until the SS attains an acceptable level. Then therapy continues with the transmission of a series of pulses and SS is measured again. If the SS has declined below an acceptable level or range, the PRF, the rate at which the pulses are transmitted, is decreased until an acceptable SS is maintained during the transmission of series of therapy pulses.

Figure 6B:
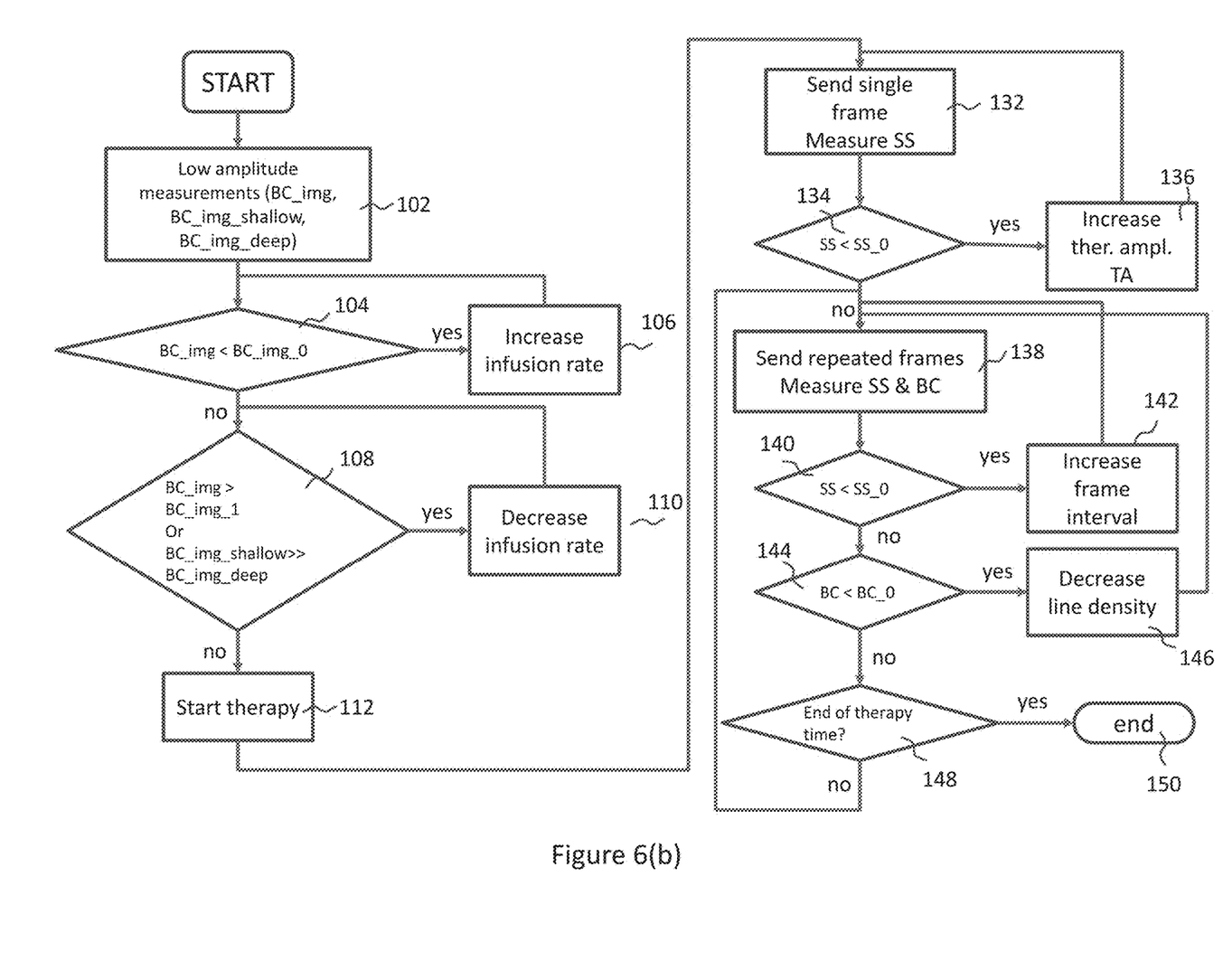
FIG. 6(b) is a flowchart of a therapy procedure conducted in accordance with the principles of the present invention when the probe is a 1D or 2D array probe which scans beams over a larger area in front of the array.

In summary, in the procedure with the array transducer, the user first optimizes the infusion rate IR under low MI transmit conditions as in the single-element procedure until the bubble concentration at the therapy ROI (BC_img) is at a favorable level. Therapy is then started, initially using a default TA. A single frame of therapy transmissions, a single series of pulses transmitted in differently steered directions across the therapy region, is transmitted and SS is measured. If SS is below an acceptable level or range, TA is increased until an acceptable level or range is achieved. Then the therapy continues with the transmission of a series of frame transmissions at an initial default frame rate FR and SS is measured again. If the SS is below an acceptable level or range, FR is decreased until an acceptable SS is maintained. If the BC drops below an acceptable level or range, LD is decreased until an acceptable BC is maintained.

FIG. 6(a) is a flowchart illustrating one example of the dynamics of therapy, bubble destruction, and bubble concentration during a typical therapeutic procedure in accordance with the present invention when a single transducer element probe is used. When a single element probe is used, the system requires no beamformer, simplifying the apparatus used for the procedure. At the start of this procedure at 102 the system makes three low amplitude measurements of bubble concentration (BC), one at the therapy site (BC_img), another at a shallower depth in the body (BC_img_shallow), and a third at a greater depth in the body (BC_img_deep). The term "img" in these notations indicates "imaging," as the amplitude or intensity of imaging pulses are generally at an MI of 0.1 or less, which is a lower instantaneous amplitude than that of many therapeutic pulses. The low amplitude BC measurement BC_img is compared with a lower threshold value for BC, BC_img_0, to see if it is below this minimally acceptable threshold. If it is, the microbubble infusion rate is increased at 106 and the measurement is repeated until the comparison 104 shows that the BC_img is at or above BC_img_0. Next, at 108, BC_img is compared to see if it is greater than BC_img_1, which is an upper acceptable threshold level for BC_img. If BC_img is above this upper acceptable threshold, the microbubble infusion rate is decreased at 110. The measurement and comparison are repeated until BC_img is below the upper acceptable threshold of BC_img_1. Another comparison which is performed in this step 108 is to see if BC_img_shallow is much greater than BC_img_deep. By "much greater" is typically meant at least 2 times. Ideally, the bubble concentration BC calculated for a shallow depth should be about the same as the bubble concentration calculated for a deeper depth, as the perfusion of microbubbles in the vasculature should be approximately the same regardless of depth in the body. If the bubble concentration at shallow depth indicates as being much greater than that at deeper depth, this indicates that the detection and hence the measurement at the deeper depth is being diminished by acoustic shadowing by microbubbles at the shallower depth, which scatters a large proportion of impinging ultrasound waves, leaving very low amounts of ultrasound available to reach the deeper depths. If a large disparity is found between the BC measurement at shallow and deep depths, e.g., more than two times, the infusion rate is decreased at 110 to reduce this acoustic shadowing which has created this disparity.

With the infusion rate being adjusted to the appropriate flow rate, therapy is started at 112. The first measurement that is made is that of sonotherapy signal strength (SS) after firing only a single pulse at 114. SS is then measured against a minimally acceptable threshold for SS, SS_0, at 116. If SS is less than SS_0, the therapeutic amplitude (TA) of the applied therapeutic ultrasound is increased at 118. Once SS has been increased above SS_0, the system starts the therapy procedure and sends repeated therapy pulses at 120. SS is then measured again and compared to the minimally acceptable threshold SS_0 at 122. If SS is less than SS_0, the pulse interval is increased at 124. Otherwise the procedure continues until end of therapy is reached at 126, 128.

FIG. 6(b) is a flowchart illustrating another example of the dynamics of therapy, bubble destruction, and bubble concentration during a typical therapeutic procedure in accordance with the present invention when an array transducer probe is used. The microbubble infusion rate is optimized in the same procedure as explained in the previous paragraph for FIG. 6(a) in 102-112. With the infusion rate being adjusted to the appropriate flow rate, therapy is started at 112. The first measurement that is made is that of sonotherapy signal strength (SS) after firing only a single frame at 132. SS is then measured against a minimally acceptable threshold for SS, SS_0, at 134. If SS is less than SS_0, the therapeutic amplitude (TA) of the applied therapeutic ultrasound is increased at 136. Once SS has been increased above SS_0, the system continues with the therapy procedure and sends repeated therapy frames at 138 and SS and BC are both measured. SS is compared again to the minimally acceptable threshold SS_0 at 140. If SS is less than SS_0, the frame interval is increased at 142. If BC is less than the minimally acceptable threshold BC_0 at 144, the line density is decreased at 146. The SS and BC comparison with their respective thresholds is repeated until they both reach the thresholds and the procedure continues until end of therapy is reached at 148, 150.

What is claimed is:

1. An ultrasonic therapy system comprising:
   an ultrasound therapy probe having an array transducer which is adapted to transmit therapeutic ultrasound energy at a therapy site in a body;
   a transmitter, coupled to the ultrasound therapy probe, which is adapted to deliver electrical energy to the array transducer to cause the array transducer to produce ultrasound probing pulses and the therapeutic ultrasound energy, wherein the transmitter is further adapted to control transmit parameters including frequency, intensity, timing and duration of the therapeutic ultrasound energy delivered by the ultrasound therapy probe;
   a source of microbubble infusion; and
   a programmed computer-based unit adapted to:
   ultrasonically measure concentration of microbubbles (BC) at the therapy site with the probing pulses and direct adjustment of the source of microbubble infusion in response to the BC measurement to maintain microbubble concentration within a target range;
   ultrasonically measure concentration of microbubbles (BC) at a first depth and at a depth deeper than the first depth and direct a decrease in an infusion rate of microbubbles from the source of microbubble infusion when the BC measurement at the first depth is much greater than the BC measurement at the deeper depth; and then
   start ultrasound therapy; and then
   measure sonotherapy signal strength (SS) as an amplitude of nonlinear signals received from a specified area in response to the therapeutic ultrasound energy delivered by the ultrasound therapy probe and direct adjustment of the intensity transmit parameter of the transmitter when the measurement of SS is below a minimally acceptable threshold for SS; and
   thereafter, when a subsequent SS measurement declines below the minimally acceptable threshold, direct the transmitter to decrease a rate at which therapy ultrasound pulses are transmitted until SS measurements are maintained within a desired therapeutic range.

2. The ultrasonic therapy system of claim 1, wherein the ultrasound therapy probe is adapted to transmit the therapeutic ultrasound energy into the body and receive echo signals from microbubbles in the body in response to the transmitted therapeutic ultrasound energy; and
   wherein the programmed computer-based unit is adapted to process echo signals received in response to the transmission of therapeutic ultrasound energy to compute the sonotherapy signal strength (SS) by detecting a maximum intensity of nonlinear echo signals received from the body in response to the transmission of therapeutic ultrasonic energy.

3. The ultrasonic therapy system of claim 1, wherein the ultrasound therapy probe is adapted to transmit the therapeutic ultrasound energy into the body and receive echo signals from microbubbles in the body in response to the transmitted therapeutic ultrasound energy; and wherein the programmed computer-based unit is adapted to process received echo signals to compute microbubbles concentration in the specified area in the body as an average signal intensity of nonlinear echo signals received from the body normalized with respect to the specified area.

4. The ultrasonic therapy system of claim 1, wherein said programmed computer-based unit is further adapted to, when a BC measurement during therapy increases above the target range of BC measurements, direct the source of microbubble infusion to decrease its flow of microbubbles.

5. The ultrasonic therapy system of claim 1,
wherein the ultrasound therapy probe is further adapted to transmit imaging pulses for imaging the therapy site, and to receive ultrasonic imaging echo signals in response to the imaging pulses;
wherein the transmitter is adapted to cause the array transducer to produce therapeutic ultrasound pulses and imaging pulses in an alternating manner; and further comprising an ultrasound imaging device, coupled to receive ultrasonic imaging echo signals from the array transducer and adapted to process the received ultrasonic imaging echo signals to produce an anatomical ultrasonic image of the therapy site in the body;
wherein the ultrasound imaging device is further adapted to display the anatomical ultrasonic image produced by the ultrasound imaging device.

6. The ultrasonic therapy system of claim 5, wherein the ultrasound therapy probe further comprises a split aperture array transducer having one sub-aperture for imaging and another sub-aperture for ultrasound therapy.

7. The ultrasonic therapy system of claim 5, wherein said programmed computer-based unit is further adapted to, when a BC measurement during therapy declines below the target range, direct the transmitter to decrease line density of transmitted ultrasound beams until BC measurements within the target range are maintained.

* * * * *